United States Patent [19]

Dinh et al.

[11] Patent Number: 5,208,358

[45] Date of Patent: May 4, 1993

[54] PROCESS FOR PREPARATION OF SILYL KETENE ACETALS

[75] Inventors: Paul C. Dinh; Jeff A. Gray; Peter Y. K. Lo, all of Midland, Mich.

[73] Assignee: Dow Corning Corporation, Midland, Mich.

[21] Appl. No.: 912,433

[22] Filed: Jul. 13, 1992

[51] Int. Cl.$^5$ .......................... C07F 7/08; C07F 7/18
[52] U.S. Cl. .................... 556/445; 556/443; 556/444; 556/448
[58] Field of Search .............. 556/445, 448, 443, 444

[56] References Cited

U.S. PATENT DOCUMENTS 4,746,750  5/1988  Neirs ................................. 556/443
4,824,981  4/1989  Schulz et al. ....................... 556/443

FOREIGN PATENT DOCUMENTS 219322  4/1987  European Pat. Off. .

OTHER PUBLICATIONS

E. Yoshii et al., Chem. Pharm. Bull. Jap. 22:2767–2769 (1974).
I. Ojima et al., J. Organometallic Chem. 111:43–60 (1976).
J. Howe et al. J. Organometallic Chem. 208:401–406 (1981).

Primary Examiner—Paul F. Shaver
Attorney, Agent, or Firm—William F. Boley

[57] ABSTRACT

The present invention is a process for preparation of silyl ketene acetals. The process comprises contacting a mixture containing an organosilane having a silicon-bonded hydrogen (organohydrosilane) and a vinylic compound with RhCl(di-tert-butylsulfide)$_2$ as catalyst at a temperature within a range of about 20° C. to 100° C. The RhCl(di-tert-butylsulfide)$_2$ catalyst demonstrates higher activity than that typically described for rhodium catalysts, allowing for lower concentrations of catalyst and lower reaction temperatures to be used while maintaining high conversion to the desired silyl ketene acetals.

15 Claims, No Drawings

PROCESS FOR PREPARATION OF SILYL KETENE ACETALS

BACKGROUND OF INVENTION

The present invention is a process for the preparation of silyl ketene acetals. The process comprises contacting a mixture comprising an organosilane having a silicon-bonded hydrogen (organohydrosilane) and a vinylic compound with RhCl(di-tert-butylsulfide)$_2$ as catalyst at a temperature within a range of about 20° C. to 100° C. The RhCl(di-tert-butylsulfide)$_2$ catalyst demonstrates higher activity than that typically described for rhodium catalysts, allowing for lower concentrations of catalyst and lower reaction temperatures to be used while maintaining high conversion to the desired silyl ketene acetals.

E. Yoshii et al.. Chem. Pharm. Bull. Jap. 22:2767-2769 (1974), describe the use of tris(triphenylphosphine)-chlororhodium as catalyst for the hydrosilation of several methyl 2-alkenoates with trialkysilanes. The process was run at 60° C. to 100° C. and a typical catalyst concentration was about $3 \times 10^{-3}$ mole percent. Typical yields of the process for silyl ketene acetals were reported to be in the range of about 31 percent to 77 percent.

I. Ojima et al., J. Organometallic Chem. 111:43-60 (1976). also describe the use of tris(triphenylphosphine)-chlororhodium as a catalyst for the hydrosilation of several methyl 2-alkenoates with trialkylsilanes. The times evaluated varied from one to 12 hours, the temperature from 40° C. to 100° C., and catalyst concentration from about 0.05 to 0.1 mole percent. Unlike Yoshii et al., Ojima et al. observed in addition to the silyl ketene acetals minor quantities of a 1,2-adduct.

J. Howe et al., J. Organometallic Chem. 208:401-406 (1981), describe two phosphine-rhodium(II) complexes found to be active catalyst for the hydrosilylation of a variety of organic substrates. The phosphine rhodium-(II) complexes are bis(tris-o-tolylphosphine)dichlororhodium(II) and bis(tricyclohexylphosphine)dichlororhodium(II). The process described by Howe et al. was conducted at 100° C. for eight hours, with catalyst concentrations in a range of about 0.4 to 0.6 mole percent.

Revis. EPO-219,322, Pub. Apr. 22, 1987, discloses a process for the manufacture of increasing yields of high-purity silyl ketene acetals, the process comprising the contacting of methacrylic acid or an ester of methacrylic acid with a hydrogen-containing silicon material in the presence of a catalyst comprising rhodium complexed with inorganic ligands. The preferred process parameters were reported to be a temperature between 40° C. to 60° C., a concentration of rhodium between 200 and 3000 ppm, and a reaction time greater than about one hour.

SUMMARY OF INVENTION

The present invention is a process for preparation of silyl ketene acetals. The process comprises contacting a mixture containing an organosilane having a silicon-bonded hydrogen (organohydrosilane) and a vinylic compound with RhCl(di-tert-butylsulfide)$_2$ as catalyst at a temperature within a range of about 20° C. to 100° C. The RhCl(di-tert-butylsulfide)$_2$ catalyst demonstrates higher activity than that typically described for rhodium catalysts, allowing for lower concentrations of catalyst and lower reaction temperatures to be used while maintaining high conversion to the desired silyl ketene acetals.

DESCRIPTION OF INVENTION

The present invention is a process for preparation of silyl ketene acetals. The process comprises:

(A) contacting a mixture comprising a organohydrosilane described by formula $$R_3SiH \tag{1}$$

and a vinylic compound described by formula $$H_2C=CR^1-COOR^2 \tag{2}$$

with RhCl(di-tert-butylsulfide)$_2$ catalyst at a temperature within a range of about 20° C. to 100° C.; and (B) recovering silyl ketene acetals described by formula $$R^1_2CHCR^1=C(OSiR_3)(OR^2); \tag{3}$$

where each R is a radical independently selected from a group consisting of alkyls comprising one to 20 carbon atoms alkoxys comprising one to 20 carbon atoms, cycloalkyls comprising four to 20 carbon atoms halogenated hydrocarbons comprising one to 20 carbon atoms, aryls and aryloxys; each $R^1$ is independently selected from a group consisting of R and hydrogen; and $R^2$ is selected from a group consisting of alkyls comprising one to 20 carbon atoms halogenated hydrocarbons comprising one to 20 carbon atoms, aryls, triorganosilyl radicals described by formula —$SiR_3$ where R is as previously described, organooxy radicals described by formula —$(CH_2)_nOR^3$ where n is an integer from one to ten and $R^3$ is selected from a group consisting of alkyls comprising one to 20 carbon atoms, cycloalkyls comprising four to 20 carbon atoms, halogenated hydrocarbons comprising one to 20 carbon atoms, aryls, and triorganosilyl radicals described by formula —$SiR_3$ and R is as previously described.

The present process can be run in any standard reactor for contacting a mixture and catalyst. The process can be run as a continuous process or as a batch process. Preferred is a continuous process conducted in a stirred-tank reactor. For best results, it is preferred that the reactor be purged with an inert gas, such as nitrogen gas containing two volume percent oxygen, prior to addition of the reactants.

The reactants can be added to the reactor either as a preformed mixture or individually. When the process is run as a batch process, it is preferred that the vinylic compound, free radical inhibitor if used, and RhCl(di-tert-butylsulfide)$_2$ catalyst be added to the reactor to form an initial mixture, then the organohydrosilane be added to this initial mixture at a controlled rate. By "controlled rate" it is meant that the organohydrosilane is added to the reactor at a rate to maintain the temperature of the mixture within the desired range. The rate of addition of the organohydrosilane will depend upon such factors as the size of the reactor, chemical formula of reactants, and the use of alternative temperature control means. Organohydrosilanes useful in the present invention are described by formula (1). The organohydrosilane contains three substituents R, where each R is a radical independently selected from a group consisting of alkyls comprising one to 20 carbon atoms, alkoxys comprising one to 20 carbon atoms, cycloalkyls comprising four to 20 carbon atoms, halogenated hydrocarbons comprising one to 20 carbon atoms, aryls, and aryloxys. The radical R can be, for example, methyl, ethyl, propyl, iso-butyl, tert-butyl, pentyl, cyclopentyl, cyclohexyl, 3,3,3-trifluoropropyl, perfluoropropyl, chloromethyl, phenyl, tolyl, xylyl, napthyl, and phenoxy. Preferred is when R is an alkyl comprising one to six carbon atoms. Most preferred is when R is methyl.

Vinylic compounds useful in the present process are described by formula (2). The vinylic compound contains substituents $R^1$, where each $R^1$ is independently selected from a group consisting of R and hydrogen and R is as previously described.

The vinylic compound contains substituent $R^2$, where $R^2$ is selected from a group consisting of alkyls comprising one to 20 carbon atoms, halogenated hydrocarbons comprising one to 20 carbon atoms, aryls, triorganosilyl radicals described by formula $-SiR_3$ where R is as previously described, and organooxy radicals described by formula $-(CH_2)_nOR^3$ where n is an integer from one to ten and $R^3$ is selected from a group consisting of alkyls comprising one to 20 carbon atoms, cycloalkyls comprising four to 20 carbon atoms, halogenated hydrocarbons comprising one to 20 carbon atoms, aryls, and triorganosilyls of formula $-SiR_3$ and R is as previously described. $R^2$ can be, for example, methyl, ethyl, phenyl, trimethylsilyl, trimethoxysilyl, dimethylphenylsilyl, and trimethylsilylethoxy. Preferred is when $R^2$ is selected from a group consisting of methyl, trimethylsilyl, and trimethylsilylethoxy.

The organohydrosilane is added to the process at a concentration of about stoichiometric equivalence to about 20 mole percent excess in relation to the vinylic compound. Preferred is when the organohydrosilane is added to the process at a concentration of about one to five mole percent excess.

The present process can employ a free radical inhibitor that is effective in preventing polymerization of the vinylic compound used in the process. In a preferred process, the free radical inhibitor is combined with the vinylic compound prior to forming a mixture of the vinylic compound with the organohydrosilane. The free radical inhibitor can be, for example, 2,6-di-tert-butyl-4-methylphenol (BHT), hydroquinone, and hydroquinone monomethyl ether.

The concentration of free radical inhibitor added to the process is that effective in reducing or preventing polymerization of the vinylic compound and will be dependent upon the particular free radical inhibitor employed. When the free radical inhibitor is BHT, a useful concentration of the free radical inhibitor is within a range of about 0.001 to 0.002 mol of BHT per mole of vinylic compound.

The catalyst employed in the present process is RhCl(di-tert-butylsulfide)$_2$ i.e. RhCl{((CH$_3$)$_3$C)$_2$S}$_2$ The RhCl(di-tert-butylsulfide)$_2$ catalyst is added to the process at a concentration within a range of about 20 ppm to 300 ppm. based on the concentration of rhodium. A preferred concentration of the catalyst is within a range of about 50 to 200 ppm, based on the concentration of rhodium. The RhCl(di-tert-butylsulfide)$_2$ catalyst can be prepared by standard procedures for reacting RCl$_3$ and di-tert-butylsulfide.

The present process can be conducted at a temperature within a range of about 20° C. to 100° C. Preferred is a temperature within a range of about 40° C. to 70° C.

The mixture comprising the organohydrosilane and vinylic compound is contacted with the RhCl(di-tert-butylsulfide)$_2$ catalyst for a time period of about 0.1 hour to ten hours. Preferred is a contact time of about 0.5 hour to five hours. Most preferred is a contact time of about 0.75 hour to two hours.

Silyl Ketene acetals (SKAs) as described by formula (3) are recovered from the present process. Recovery of the SKAs can comprise storing or using the SKAs without further treatment or can comprise further processing, for example distillation, to separate the SKAs from unreacted feed materials and by-products.

The following examples are offered to illustrate the present invention. These examples are not intended to limit the claims provided herein.

EXAMPLE 1

The specificity of RhCl(di-tert-butylsulfide)$_2$ to catalyze the reaction of trimethylsilane with methylmethacrylate to form trimethylsilyldimethyl-ketene acetal was evaluated. The reactor consisted of a 500-mL flask equipped with a dry-ice condenser, a magnetic stirrer, and a thermometer. The reactor was charged with 111 g of methylmethacrylate (MMA), 1.23 g of a toluene solution containing 0.0285 g of RhCl(di-tert-butylsulfide)$_2$ catalyst, and 0.297 g of 2,6-di-tert-butyl-4-methylphenol (BHT). This mixture was stirred and heated to 55° C. under a constant purge with a 2% oxygen and 98% nitrogen mixture. After the mixture reached 55° C., heat was removed and 107 g trimethylsilane (Me$_3$SiH) was fed to the reactor as a gas. The cumulative stoichiometric amount of trimethylsilane added at the end of each sampling period is provided in Table 1 in the column labelled "%Me$_3$SiH." The trimethylsilane feed rate was regulated to maintain the temperature within the reactor at 55° C. to 60° C. Samples were taken during the course of the trimethylsilane addition to analyze for product formation. These samples are identified in Table 1 as samples 1 through 5 and the corresponding time for collecting the sample after the initiation of addition of trimethylsilane is given in the column labelled "Time." Each sample was analyzed using gas chromatography with a mass spectrometer as detector (GC/MS). The results are presented in Table 1 as the area percent under the GC/MS trace for each of the following: MMA, trimethylsilyldimethyl-ketene acetal i.e.
(CH$_3$)$_2$C=C(OMe)(OSiMe$_3$), labelled SKA1;
H$_2$C=C(CH$_3$)CH(OMe)(OSiMe$_3$), labelled CA1, and
Me$_3$SiCH$_2$C(CH$_3$)HCOOMe, labelled VA1.

TABLE 1

| | RhCl(di-tert-butylsulfide)$_2$ Catalyzed Reaction of Trimethylsilane With Methylmethacrylate | | | | | |
|---|---|---|---|---|---|---|
| Sample No. | Time (h) | % Me$_3$SiH | GC/MS Area percent | | | |
| | | | MMA | SKA1 | CA1 | VA1 |
| 1 | 0.3 | 10 | 71.0 | 16.0 | 2.8 | 0.2 |
| 2 | 1.2 | 36 | 32.5 | 38.4 | 6.4 | 0.3 |
| 3 | 2.2 | 72 | 7.9 | 71.0 | 10.0 | 0.4 |
| 4 | 3.0 | 92 | 1.4 | 75.0 | 6.9 | 0.6 |
| 5 | 3.5 | 110 | 0.1 | 80.5 | 4.6 | 0.7 |

EXAMPLE 2

A comparison of the specificity of RhCl(di-tert-butylsulfide)$_2$ and RhCl$_3$3H$_2$O to catalyze the reaction of trimethylsilane with trimethylsilyl-hydroxyethylmethacrylate (TMS-HEMA) to form O-trimethylsilyl-O- trimethysilyl-hydroxyethylmethacrylate (SKA2) was evaluated.

In a first run, 290 g of TMS-HEMA, 1.34 g of toluene solution containing 0.039 g of RhCl(di-tert-butylsulfide)$_2$, and 0.16 g of BHT were added to the same reactor as described in Example 1. This mixture was stirred and heated to 55° C. under a constant purge with a 2% oxygen and 98% nitrogen mixture. After the mixture reached 55° C., heat was removed and 117 g of trimethylsilane fed to the reactor as a gas. The trimethylsilane feed rate was regulated to maintain the temperature within the reactor a 55° C. to 60° C. The cumulative stoichiometric amount of trimethylsilane added at the end of each sampling period is provided in Table 2 in the column labelled "%Me$_3$SiH." Samples were taken at various times during addition of the trimethylsilane and analyzed by GC/MS, as described in Example 1. The results are presented in Table 2a as the area percent under the GC/MS trace for each of the following: TMS-HEMA i.e.
$H_2C=C(CH_3)COO(CH_2)_2OSi(CH_3)_3$;
$(CH_3)_2C=C\{OSi(CH_3)_3\}\{O(CH_2)_2OSi(CH_3)_3\}$, labelled SKA 2;
$H_2C=C(CH_3)CH\{OSi(CH_3)_3\}\{O(CH_2)_2OSi(CH_3)_3\}$, labelled CA2; and
$(CH_3)_3SiCH_2CH(CH_3)COO(CH_2)_2OSi(CH_3)_3$, labelled VA2.

TABLE 2a

RhCl(di-tert-butylsulfide)$_2$ Catalyzed Reaction of Trimethylsilane With TMS-HEMA

| Sample No. | Time (h) | % Me$_3$SiH | GC/MS Area Percent | | | |
|---|---|---|---|---|---|---|
| | | | TMS-HEMA | SKA2 | CA2 | VA2 |
| 1 | 0.4 | 20 | 75.5 | 19.4 | 1.7 | 0.0 |
| 2 | 0.75 | 40 | 53.1 | 39.2 | 3.5 | 0.0 |
| 3 | 1.0 | 60 | 36.1 | 52.3 | 5.0 | 0.1 |
| 4 | 1.3 | 80 | 19.5 | 73.7 | 6.9 | 0.1 |
| 5 | 1.75 | 110 | 4.1 | 79.5 | 7.8 | 0.1 |
| 6 | 3.0 | 110 | 0.4 | 84.3 | 7.5 | 0.2 |
| 7 | 6.0 | 110 | 0.2 | 85.4 | 7.9 | 0.1 |

A comparison run, using 0.0188 g of RhCl$_3$.3H$_2$O dissolved in 0.127 g of methanol as catalyst, was conducted in the same manner as described for the first run. The results are provided in Table 2b. The headings of Table 2b are as described for Table 2a.

TABLE 2b

RhCl$_3$.3H$_2$O Catalyzed Reaction of Trimethylsilane With TMS-HEMA

| Sample No. | Time (h) | % Me$_3$SiH | GC/MS Area Percent | | | |
|---|---|---|---|---|---|---|
| | | | TMS-HEMA | SKA2 | CA2 | VA2 |
| 1 | 2.2 | 50 | 54.9 | 35.2 | 3.4 | 0.1 |
| 2 | 3.2 | 80 | 18.0 | 64.4 | 6.0 | 1.2 |
| 3 | 4.0 | 91 | 9.8 | 63.5 | 5.9 | 1.9 |
| 4 | 8.0 | 110 | 9.0 | 67.4 | 6.7 | 2.5 |

The results of this comparison demonstrate that RhCl(di-tert-butylsulfide)$_2$ causes the desired SKA2 to be formed at a faster rate and results in a higher SKA2 to VA2 ratio, when compared to the RhCl$_3$.3H$_2$O catalyzed process.

EXAMPLE 3

The effect of the concentration of RhCl(di-tert-butylsulfide)$_2$ on the reaction of trimethylsilane with trimethylsilyl-methacrylic acid (TMS-MA) was evaluated in a series of runs. All runs in this series followed the following general procedure. To the reactor described in Example 1 was added 98.6 g of TMS-MA, RhCl(di-tert-butylsulfide)$_2$ at a concentration as described in Table 3. and 0.284 g of BHT. This mixture was stirred and heated to 60° C. under a constant purge with a 2% oxygen and 98% nitrogen mixture. After the mixture reached 60° C., heat was removed and 50.8 g of trimethylsilane was fed to the reactor as a gas. The trimethylsilane feed rate was regulated to maintain the temperature within the reactor at 55° C. to 60° C. A sample for analysis was taken at the times indicated in Table 3, for each concentration of RhCl(di-tert-butylsulfide)$_2$ tested. The concentrations are presented in Table 3 as parts per million rhodium. Each sample was analyzed by GC/MS and the results are reported in Table 3 as area percent under the GC/MS trace for each of the following: TMS-MA i.e.
$CH_2=C(CH_3)COOSi(CH_3)_3$;
$(CH_3)_2C=C\{OSi(CH_3)_3\}_2$, labelled SKA3;
$H_2C=C(CH_3)CH\{OSi(CH_3)_3\}_2$, labelled CA3: and
$(CH_3)_3SiCH_2CH(CH_3)COOSi(CH_3)_3$, labelled VA3.

TABLE 3

Effect of RhCl(di-tert-butylsulfide)$_2$ Concentration on Reaction of Trimethylsilane With TMS-MA

| RUN No. | Time (h) | PPM Rh | GC/MS Area Percent | | | |
|---|---|---|---|---|---|---|
| | | | TMS-MA | SKA3 | CA3 | VA3 |
| 1 | 4.0 | 50 | 40.8 | 44.1 | 2.1 | 0.7 |
| 2 | 4.0 | 100 | 1.2 | 80.6 | 3.9 | 0.6 |
| 3 | 3.5 | 150 | 3.9 | 78.1 | 3.7 | 0.1 |
| 4 | 4.0 | 200 | 2.1 | 79.5 | 4.6 | 0.3 |
| 5 | 3.0 | 250 | 10.8 | 79.4 | 3.9 | 0.1 |

I claim:
1. A process for preparation of silyl ketene acetals, the process comprising:
(A) contacting a mixture comprising a organohydrosilane described by formula

$R_3SiH$ and a vinylic compound described by formula $R^1_2C=CR^1-COOR^2$ with RhCl(di-tert-butylsulfide)$_2$ catalyst at a temperature within a range of about 20° C. to 100° C.; and
(B) recovering a silyl ketene acetal described by formula $R^1_2CHCR^1=C(OSiR_3)(OR^2)$;

where each R is a radical independently selected from a group consisting of alkyls comprising one to 20 carbon atom, alkoxys comprising one to 20 carbon atoms, cycloalkyls comprising four to 20 carbon atoms, halogenated hydrocarbons comprising one to 20 carbon atoms, aryls, and aryloxys; each $R^1$ is independently selected from a group consisting of R and hydrogen; and $R^2$ is selected from a group consisting of alkyls comprising one to 20 carbon atoms, halogenated hydrocarbons comprising one to 20 carbon atoms, aryls, triorganosilyl radicals described by formula —SiR$_3$ where R is as previously described, and organooxy radicals of formula —(CH$_2$)$_n$OR$^3$ where n is an integer from one to ten and $R^3$ is selected from a group consisting of alkyls comprising one to 20 carbon atoms, cycloalkyls comprising four to 20 carbon atoms, halogenated hydrocarbons comprising one to 20 carbon atoms, aryls, and triorganosilyls described by formula —SiR$_3$ and R is as previously described.

2. A process according to claim 1, where R is an alkyl comprising one to six carbon atoms.

3. A process according to claim 1, where R$^2$ is selected from a group consisting of methyl, trimethylsilyl, and trimethylsilylethoxy.

4. A process according to claim 1, where the organohydrosilane is added to the process at a concentration of about one to five mole percent excess in relation to the vinylic compound.

5. A process according to claim 1 further comprising the addition of a free radical inhibitor.

6. A process according to claim 5, where the free radical inhibitor is combined with the vinylic compound prior to forming the mixture of the vinylic compound with the organohydrosilane.

7. A process according to claim 6, where the free radical inhibitor is selected from a group consisting of 2,6-di-tert-butyl-4-methylphenol, hydroquinone, and hydroquinone monomethyl ether.

8. A process according to claim 1, where the concentration of RhCl(di-tert-butylsulfide)$_2$ is within a range of about 50 to 200 ppm.

9. A process according to claim 1, where the temperature is within a range of about 40° C. to 70° C.

10. A process according to claim 1, where contact of the mixture with RhCl(di-tert-butylsulfide)$_2$ catalyst is for a time of about 0.5 hour to five hours.

11. A process according to claim 1, where contact of the mixture with RhCl(di-tert-butylsulfide)$_2$ catalyst is for a time of about 0.75 hour to two hours.

12. A process according to claim 1, where R is an alkyl comprising one to six carbon atoms; R$^2$ is selected from a group consisting of methyl, trimethylsilyl, and trimethylsilylethoxy: the organohydrosilane is added to the process at a concentration of about one to five mole percent excess in relation to the vinylic compound; the temperature is within a range of about 40° C. to 70° C.; and contact of the mixture with the RhCl(di-tert-butylsulfide)$_2$ catalyst is for a time of about 0.75 hour to two hours.

13. A process according to claim 12 further comprising the addition of a free radical inhibitor.

14. A process according to claim 13, where the free radical inhibitor is combined with the vinylic compound prior to forming the mixture of the vinylic compound with the organohydrosilane.

15. A process according to claim 14, where the free radical inhibitor is 2,6-di-tert-butyl-4-methylphenol.

* * * * *